United States Patent [19]

Alderson

[11] Patent Number: 4,711,246
[45] Date of Patent: Dec. 8, 1987

[54] FIBER OPTIC COUPLED PRESSURE TRANSDUCER USING SINGLE FIBER AND METHOD OF FABRICATION

[75] Inventor: Richard Alderson, Phoenix, Ariz.

[73] Assignee: Fiberoptic Sensor Technologies, Inc., Ann Arbor, Mich.

[21] Appl. No.: 902,666

[22] Filed: Sep. 2, 1986

[51] Int. Cl.⁴ .............................................. A61B 5/02
[52] U.S. Cl. ................................. 128/667; 128/675; 128/748; 73/705
[58] Field of Search ................. 128/664–667, 128/672–673, 675, 748, 634; 73/705, 708, 715

[56] References Cited

U.S. PATENT DOCUMENTS

| | | | |
|---|---|---|---|
| 3,215,135 | 11/1965 | Franke | 128/675 |
| 3,249,105 | 5/1966 | Polanyi | 128/675 |
| 3,267,932 | 8/1966 | Valliere | 128/675 |
| 3,273,447 | 9/1966 | Frank | 128/675 X |
| 4,201,222 | 5/1980 | Haase | 128/666 X |
| 4,487,206 | 12/1984 | Aagard | 128/673 X |
| 4,593,701 | 6/1986 | Kobayashi et al. | 128/667 |

FOREIGN PATENT DOCUMENTS 0079086 5/1983 European Pat. Off. .

OTHER PUBLICATIONS

Delannois, "Low Cost IC Transducer for Medical Pressure Measurements", Med. and Biol. Engr., vol. 12, No. 3, 5–1974, pp. 364–365.

Primary Examiner—William E. Kamm
Assistant Examiner—Angela D. Sykes
Attorney, Agent, or Firm—Charles S. McGuire

[57] ABSTRACT

A miniaturized pressure transducer is disclosed wherein light transmitted through a single optical fiber is reflected by a diaphragm exposed to and deflected in accordance with the pressure being measured. The terminal end of the fiber is covered by a light absorption layer having a plurality of discrete openings through which light may pass for reflection by the diaphragm with the proportion of light passing back through the openings and the fiber varying in accordance with the distance between the end of the fiber and the diaphragm, as determined by the pressure exerted thereon. The diaphragm is incorporated in a disposable tip which is threaded to an elongated tube which holds a ferrule containing the fiber and fixedly positioning the terminal end thereof for predetermined spacing from the diaphragm. The disclosure also includes a novel method of mass producing the end-coated fibers in assembled relation with the ferrules.

10 Claims, 12 Drawing Figures

FIG. 2A  250 μm FIBER

FIG. 2B  250 μm FIBER

FIBER OPTIC COUPLED PRESSURE TRANSDUCER USING SINGLE FIBER AND METHOD OF FABRICATION

BACKGROUND OF THE INVENTION

The present invention relates to fiber optic coupled pressure transducers and to methods of fabrication thereof. More specifically, the invention relates to miniaturized pressure measurement apparatus, such as intravascular catheter tip fiber optic pressure sensors, and to mass production techniques permitting low unit cost production of such apparatus.

Measurement of intravascular blood pressure by means of a hollow catheter tube filled with saline solution and attached to an external transducer has been largely supplanted by fiber optic coupled catheter tips incorporating a pressure transducer. The prior art encompassing the latter includes fiber optic pressure sensors in which a reflecting, pressure deformable diaphragm at the end of a catheter tip is spaced a small distance from the end of a fiber bundle and modulates the light reflected back through the fibers in accordance with the pressure responsive position of the diaphragm.

An example of such a catheter tip pressure sensor is shown in U.S. Pat. No. 4,487,206 wherein three optic fibers extend through a hollow catheter tube to a lens element at the terminal ends of the fibers within a sensor tip. Light transmitted from a source outside the tube through one fiber is directed to a pressure responsive, reflecting surface which modulates the focal length of the lens-mirror-diaphragm combination. Light returning through the other two fibers is sensed by reference and signal sensor detectors, respectively, permitting the development of a pressure-indicative signal. It is desirable, of course, to make the catheter tubes and tips as small as possible in such applications, provided the required level of accuracy and reliability of operation are maintained. Also within the necessary limits of accuracy and reliability, the apparatus should be as simple and economical as possible to fabricate, operate and service.

It is a principal object of the present invention to provide a fiber optic coupled pressure transducer of extremely small diameter which is easy and relatively cheap to manufacture and, at the same time, highly accurate and reliable.

It is a further object to provide a miniaturized, intravascular, fiber optic pressure sensor which may be fabricated at a cost which permits disposal of portions of the sensor after each use.

A more specific object is to provide a fiber optic coupled pressure measurement system requiring only a single optic fiber for carrying light both transmitted to and reflected from a pressure responsive diaphragm.

Still another object is to provide a disposable (single use) intravascular catheter tip of compact design which is defibrillator proof, with low artifact generation and relatively broad manufacturing tolerances.

A still further object is to provide a novel method of manufacturing fiber optic catheter tips for use in intravascular blood pressure monitoring.

Another object is to provide a fiber optic, intravascular, blood pressure measuring unit which is compatible with all currently available monitors, irrespective of the type of excitation voltage supplied.

Other objects will in part be obvious and will in part appear hereinafter.

SUMMARY OF THE INVENTION

In accordance with the foregoing objects, the present invention contemplates a fiber optic coupled pressure transducer having a single optical fiber which simulates the function of a bundle of such fibers with commensurate sensitivity and accuracy. One end of the fiber is covered by a light absorbing coating with a plurality of discrete, light-transmitting openings, preferably of equal size and symmetrical spacing. For example, the fiber may be 250 microns in diameter with circular openings in the coating having both a diameter and spacing of approximately 5 microns.

The coated end of the fiber is permanently mounted in a central opening in a ferrule of triangular outer cross section which, in turn, is mounted in and extends from one end of a length of flexible, hollow tubing through which the fiber extends to its opposite, uncoated end. One end of a hollow, cylindrical cap is covered by a flexible diaphragm and the other end is threadedly connected to the end of the tubing, enclosing the end of the ferrule extending therefrom and positioning the coated end of the fiber at a predetermined spacing from the inside of the diaphragm. Vent channels are provided in the spaces between the flat, outer, side walls of the ferrule and the cylindrical, inside wall of the hollow tubing, permitting the inside of the diaphragm to be exposed to a known, constant pressure through the hollow tubing.

Pressure measurements are made by placing the end of the tubing carrying the cap in the desired location, e.g., by intravascular insertion to a patient's heart, and connecting the other end to an optical connector including a beam splitter. Light of known intensity is transmitted through the beam splitter and optical fiber to the coated end thereof. Light passing through the openings in the coating is reflected by the inside of the diaphragm with the amount of light passing back through the openings being a function of the distance between the diaphragm and the end of the fiber. Since the outside of the diaphragm is exposed to the pressure to be measured and, deflected in accordance therewith, measurement of the intensity of light passing back through the fiber and reflected from the beam splitter may be accurately correlated to pressure on the diaphragm.

The invention further comprises a novel manufacturing method for mass production of the end-coated optical fibers and their assembly with the ferrules. This includes cutting the individual ferrules from a continuous length of drawn tubing and loading them into a fixture plate having a large number (e.g., 2,000) of cavities for receiving and fixedly positioning the ferrules. The fibers are inserted and permanently glued into the fixture-mounted ferrules and the entire plate, including the end surfaces of all ferrules and fibers are lapped and polished in a single operation. A photo resist coating containing carbon black is then applied to cover all fiber ends to act as the light absorber at the end of the fiber. The coating is then exposed in a standard semiconductor aligning machine against a glass plate which generates the pattern of small holes in the resist material upon development. The ferrules are then unloaded from the fixture and are ready for assembly with the caps.

A unique system of electronics and automatic calibration, permitting a wide tolerance range in fabrication of the disposable part of the unit is also disclosed an an element of the invention.

BRIEF DESCRIPTION OF THE DRAWINGS

FIGS. 2A and 2B are diagrammatic illustrations of light-carrying and reflecting members, providing background for explanation of the operating principles of the present invention;

DETAILED DESCRIPTION

Figure 1:
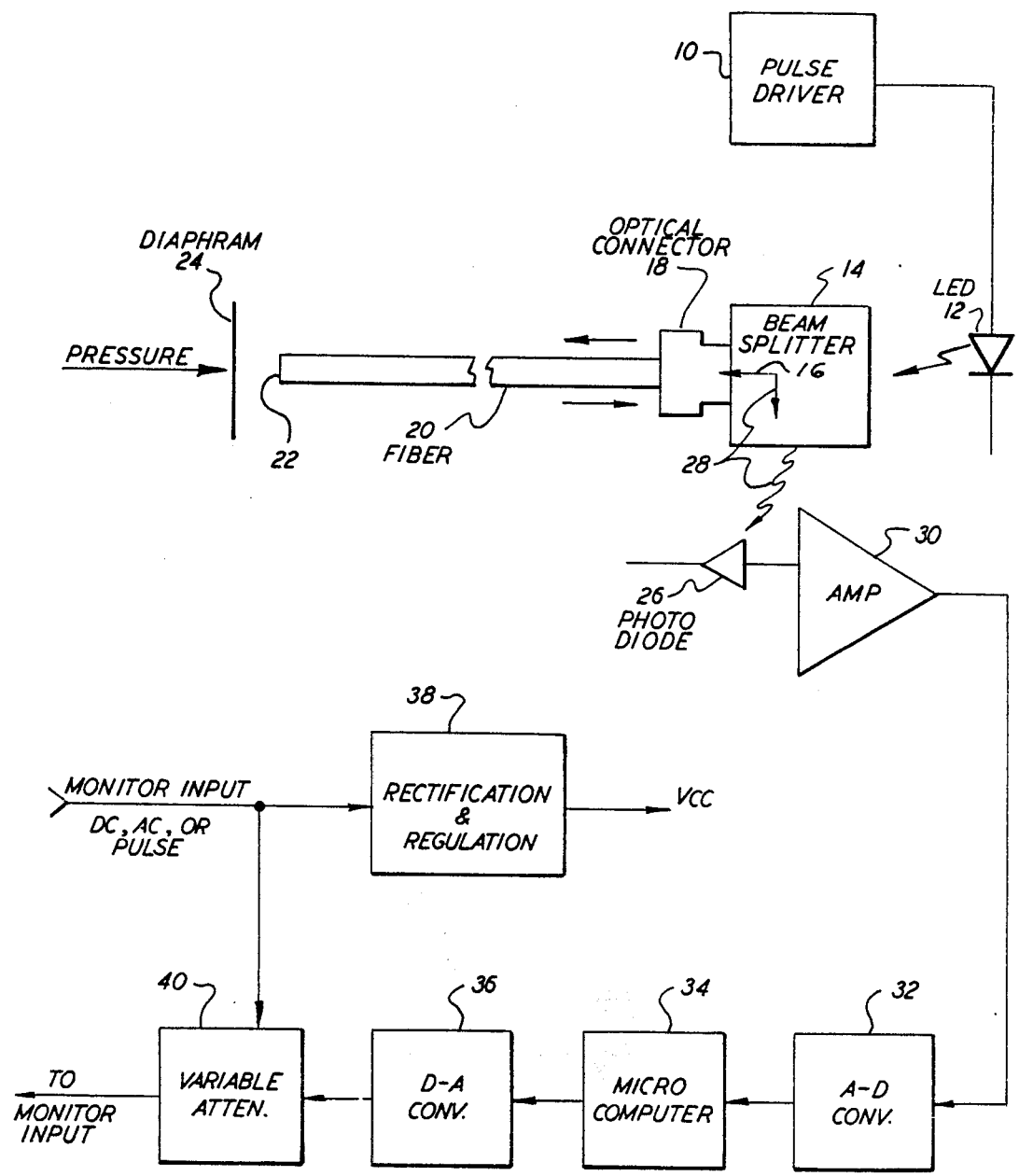
FIG. 1 is a block diagram illustrating the basic elements and general manner of operation of the pressure transducer encompassed by the present invention.

Referring now to FIG. 1, pulse generator 10 drives light emitting diode (LED) 12 to generate short pulses of very high intensity light, in conventional fashion. The light pulses passing through beam splitter 14, indicated by arrow 16, pass through optical connector 18 and travel along optical fiber 20. The light rays which exit end 22 of fiber 20 are reflected by flexible diaphragm 24 and, depending upon the angle of reflection, either pass back into fiber 20 or are "lost," i.e., reflected outside the fiber. As explained later in more detail, the amount of light reflected back into fiber 20 is a function of the distance between fiber end 22 and the reflecting surface of diaphragm 24.

A portion of the light passing back through fiber 20 is reflected by beam splitter 14 and impinges upon photodiode 26, such light being indicated by arrow 28. The resulting electrical signal from photodiode 26, as modulated by the intensity of light impinging thereon, is amplified by amplifier 30, and converted to a digital signal by A to D converter 32. The digital signal is then processed for linearity and other functions by microcomputer 34 in conventional fashion, and converted back to an analog signal by D to A converter 36.

Monitors for pressure transducers of the type with which the present invention is concerned supply excitation voltages which may be AC, DC or pulsed DC. One of the design features of the present system is that it will operate on excitation power of any known monitor. The monitor power is rectified and regulated by appropriate circuitry, indicated by block 38 to supply the operating power for the system electronics, indicated as Vcc. Monitor power is also supplied to variable attenuator 40, as is the output of D to A converter 36. The signal output of variable attenuator 40, supplied to the monitor input, is a direct representation of the excitation waveform. Thus, the signal becomes compatible with all known monitors.

Referring now to FIG. 2A, light rays A, B and C are shown passing through optical fiber F and reflected by surface R along a path dependent upon the angle of incidence of each ray upon the reflecting surface. The distance between the end of fiber F and surface R is indicated in FIG. 2A and "d" and all of rays A, B and C are reflected back into the fiber. In FIG. 2B, surface R is at distance D from the end of fiber F; although rays A, B and C exit the end of fiber F at the same angle as in FIG. 2A, ray C is not reflected back into the fiber due to the greater distance of surface R from the end of the fiber. Thus, it is seen that the light passing through fiber F is attenuated as a function of the distance of reflecting surface R from the end of the fiber.

Figure 2C:
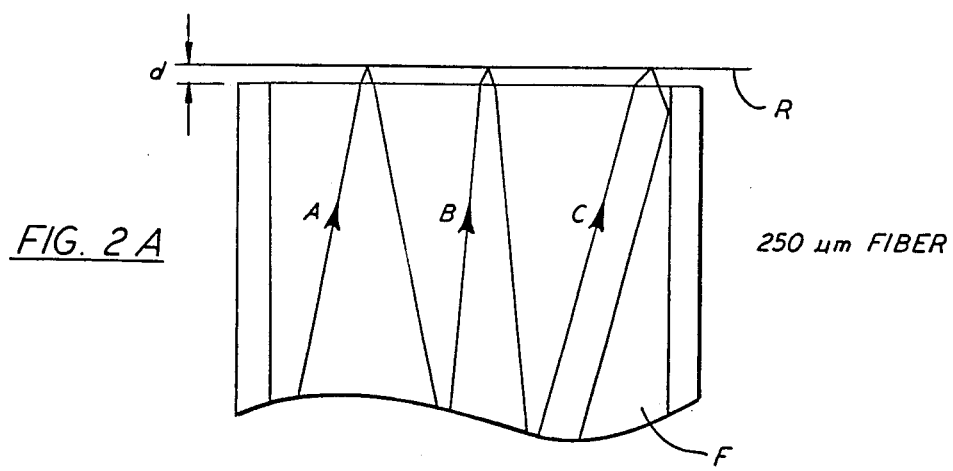
FIG. 2C is a graphical illustration of the attenuation of light passing through the light-carrying member of FIGS. 2A and 2B as a function of the distance of the reflecting surface from the end of the light-carrying member.
Figure 2C:
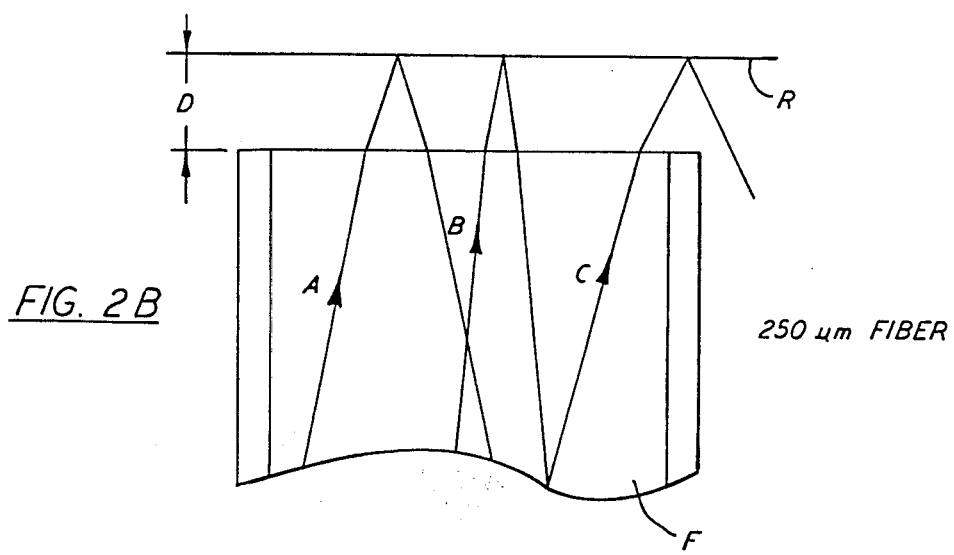
Figure 2C:
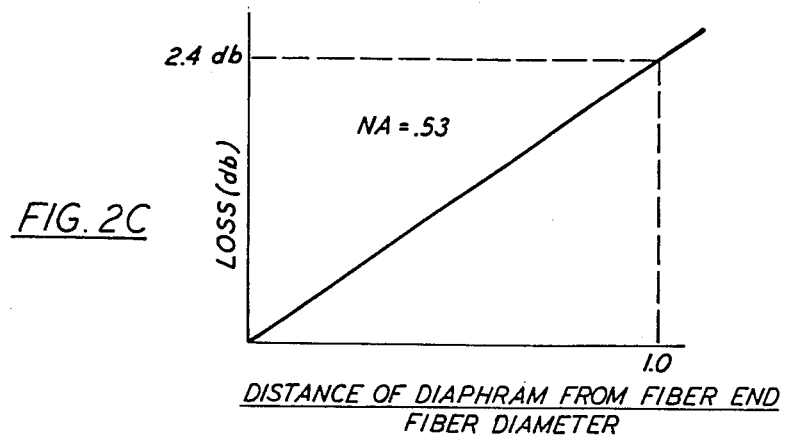

The graph of FIG. 2C illustrates the amount of attenuation of light passing through an optical fiber in relation to the distance of the reflecting surface from the fiber end. The horizontal axis represents the ratio of the distance between the reflecting surface and fiber end divided by fiber diameter, and the vertical axis represents the amount of light attenuation in decibles. The graph is based on a fiber with a diameter of 250 microns and a numerical aperture of 0.53, typical for conventional plastic optical fibers. As indicated by the graph, in order to obtain an attenuation of 2.4 db it is necessary to move the reflecting surface one fiber diameter away from the end of the fiber. In the type of pressure transducers presently under consideration, the amount of diaphragm movement necessary to achieve the required levels of sensitivity would be impractical to achieve with a single 250 micron fiber. The graph is applicable for fiber diameters down to several wavelengths, whereby a system having acceptable sensitivity have been obtained by using a bundle of many small fibers. However, fiber bundles are expensive to implement, making an alternative approach desireable.

Figure 3A:
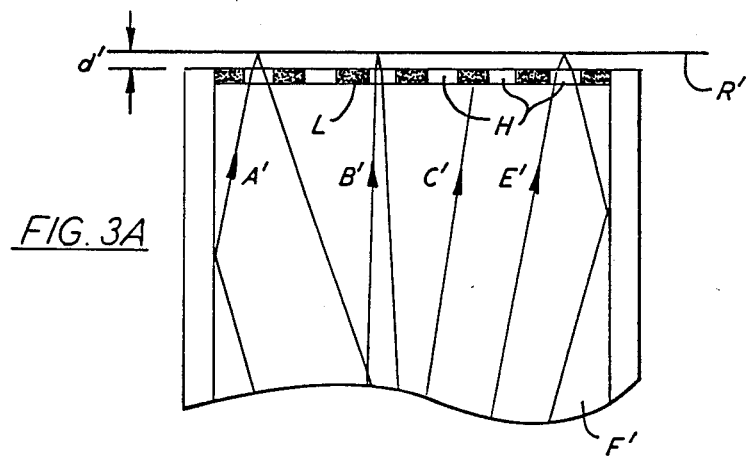
FIGS. 3A and 3B are diagrammatic illustrations of the transmission of light rays through a transparent fiber and reflection of such rays by a reflecting member positioned at two different distances from the end of the fiber in the system of the present invention.
Figure 3B:
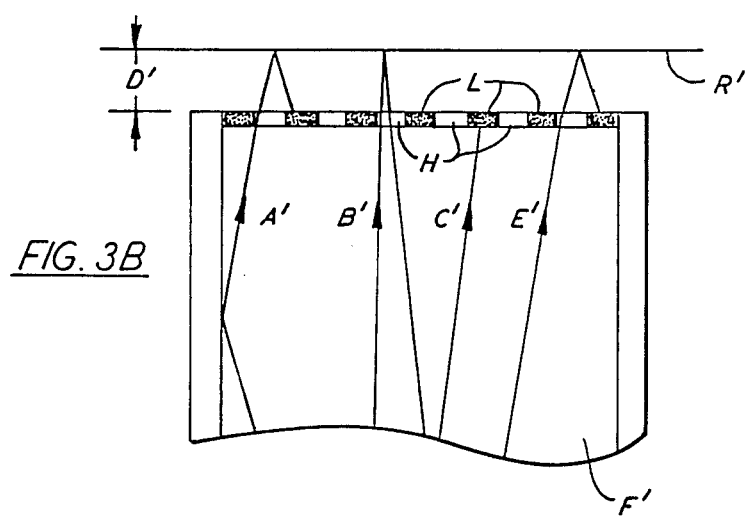

The approach to the problem which typifies the present invention is illustrated in its basic form in FIGS. 3A and 3B. Light rays A', B', C', and E' are shown passing through optic fiber F' and reflected from surface R'. Fiber F' is of the same diameter as fiber F of FIGS. 2A and 2B, differing therefrom by the addition of light absorptive layer L, having a plurality of small, clear holes H therein, applied to the end. Layer L may comprise a coating of a suitable black photo-resist material applied over the entire end of the fiber with holes H formed by known semi-conductor processes. For a 250 micron diameter fiber, holes H may be 5 microns in diameter, and spaced from one another by about 5 microns. As explained later, this may be performed in a batch process yielding, e.g., 2,000 fibers per cycle, thereby keeping the unit cost quite low.

Figure 3C:
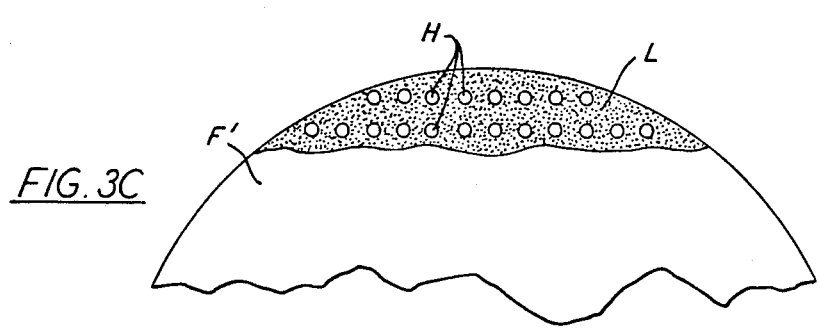
FIG. 3C is a greatly enlarged, fragmentary, plan view of a portion of one end of a light-carrying fiber incorporated in the present invention.

With reflecting surface R' positioned distance d' from the end of fiber F', as in FIG. 3A, rays A', B' and E' are reflected back into the fiber, and ray C' is intercepted by absorptive layer L and do not pass through the end of the fiber. In FIG. 3B, with surface R' moved to distance D' from the end of the fiber, only ray B' is reflected back into the fiber, rays A' and E' being reflected onto and absorbed by layer L. Thus, by providing a light absorptive coating with a plurality of clear holes on the end of a single fiber, the effect of a bundle of small fibers is simulated without the attendant cost and complexity. The end-coated fiber F' of FIGS. 3A and 3B provide a sensitivity increase of some 25 times that of an uncoated fiber F (FIGS. 2A and 2B), with a very good signal level. A fragment of the end of fiber F' with layer L applied thereto is shown in FIG. 3C.

Figure 5:
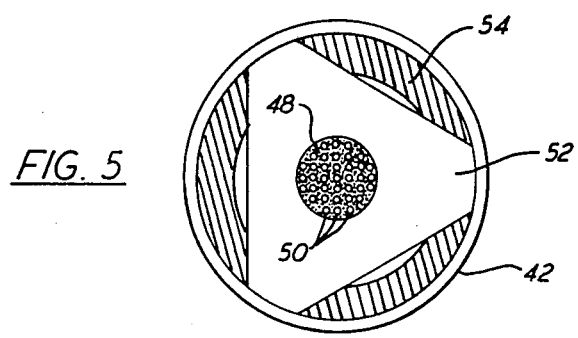
FIG. 5 is a plan view of the assembly of FIG. 4, in section on the line 5—5 thereof.
Figure 4:
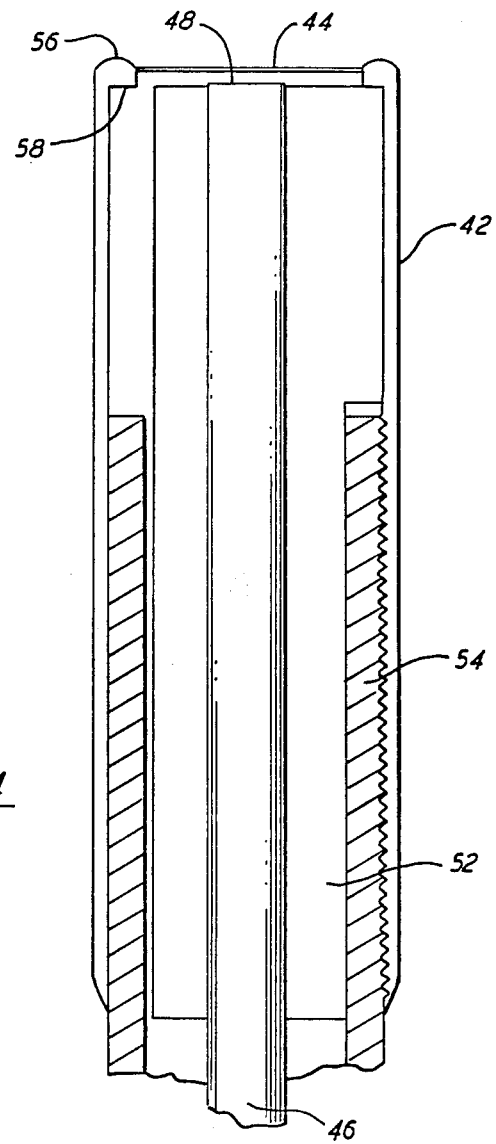
FIG. 4 is an enlarged fragmentary, side elevational view, in half section, of the transducer assembly.

Turning now to FIGS. 4 and 5, a preferred embodiment of a pressure transducer tip incorporating an end-coated fiber, suitable for use in catheter applications, is shown. The tip includes hollow, cylindrical cap 42, having one open end from which extends an internal, rolled thread, and a closed end covered by integrally formed diaphragm 44. Optical fiber 46, having a terminal end with light absorptive coating 48 applied thereto and clear holes 50 in the coating, is held firmly in a central opening in ferrule 52. As seen in FIG. 5, ferrule 52 is generally triangular in cross section, having three flat sides with the edges or corners rounded to fit tightly within cap 42. The internal thread in the open end of cap 42 is engaged with an external thread on flexible, hollow tube 54, through the entire length of which fiber 46 extends.

Cap 42 is preferably fabricated from titanium of a commercially pure variety (99.6%) which is readily available, has good body fluids compatibility, is widely accepted in the medical field, and has excellent mechanical properties for application as a pressure transducer catheter tip. Cap 42 is initially formed with a closed end of the same thickness as the side wall. The closed end is then thinned, e.g., by a hot coining process, to bring diaphragm 44 to its final desired thickness and shape, which should be flat to slightly convex with no ripples or waves which could increase its stiffness. The internal threads may then be rolled from the open end as a secondary operation. The periphery of the closed end, surrounding diaphragm 44, has rounded external lip 56 and internal shoulder 58.

Figure 6:
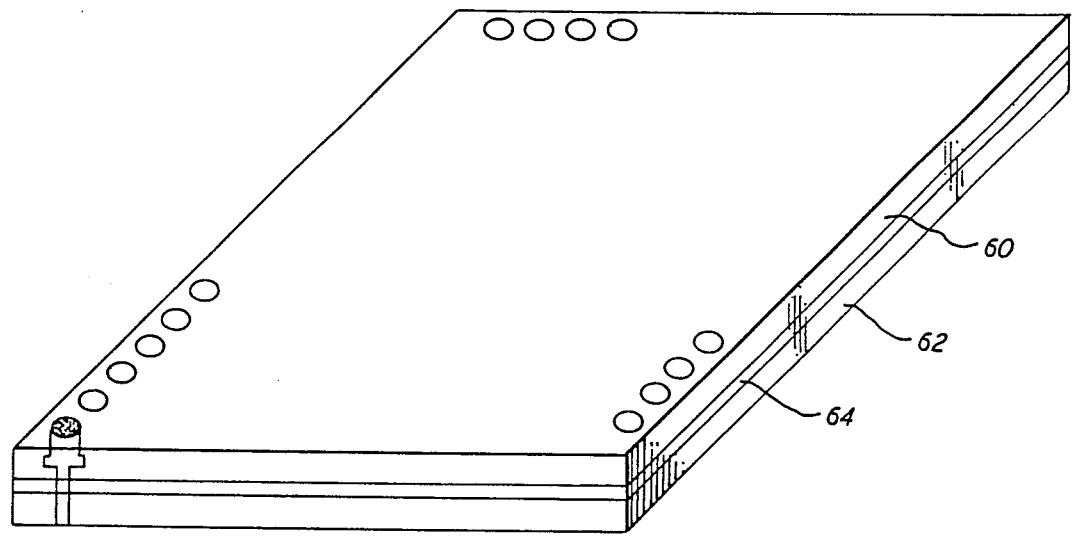
FIG. 6 is a somewhat diagrammatic, perspective view illustrating a step in the fabrication of portions of the transducer assembly.
Figure 7:
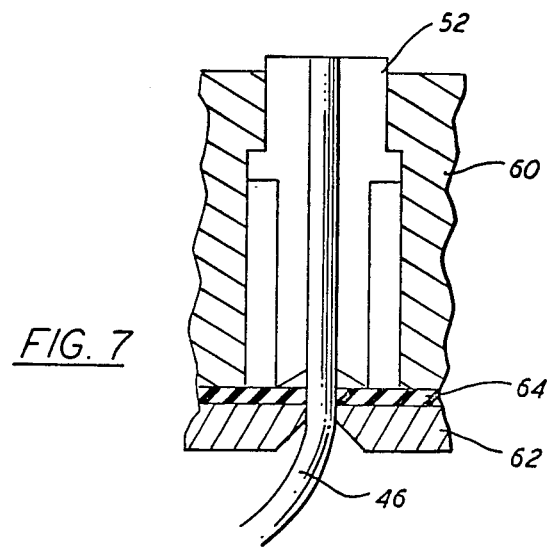
FIG. 7 is a fragmentary, enlarged, elevational view, in section on the line 7—7 of FIG. 6.

Ferrule 52 is preferably formed from drawn tubing with a central, circular opening and triangulated exterior. The continuous tubing is fed through a screw machine where it is turned, chamfered and cut off to provide the individual parts. The cut-off burr will provide a stop for the fibers as they are inserted into the central openings in the ferrules. The preferred method of fabricating the end-coated fibers with ferrules on the end is illustrated in FIGS. 6 and 7. Individual ferrules 52 are loaded in appropriately sized openings in a work fixture comprising fixture plate 60 and clamp plate 62 with shim 64 of rubber or other resilient material placed between the two to accommodate small variations in ferrule length. Fibers 46 are permanently affixed in the ferrule openings by glue applied with an auto glue injector. For parts of the size contemplated, a 4×4 inch fixture would hold up to about 2,000 parts.

The entire plate, including the exposed upper ends of the ferrules and fibers is then lapped and polished, insuring that the ends of the fibers are flat and the ends of the fibers are polished to a good optical finish. The light absorptive coating, consisting of a photo-resist material with a sufficient amount of carbon black to provide the desired absorptive properties, is then applied. The coating is then exposed in a standard, semiconductor aligning machine against a glass plate to generate the pattern of small holes in the resist material upon development. After development the ferrules and fibers are unloaded from the fixture and are ready for assembly with cap 42. Internal shoulder 58 provides a stop positioning ferrule 52 with the coated end of fiber 46 at the proper distance from diaphragm 44.

Figure 8:
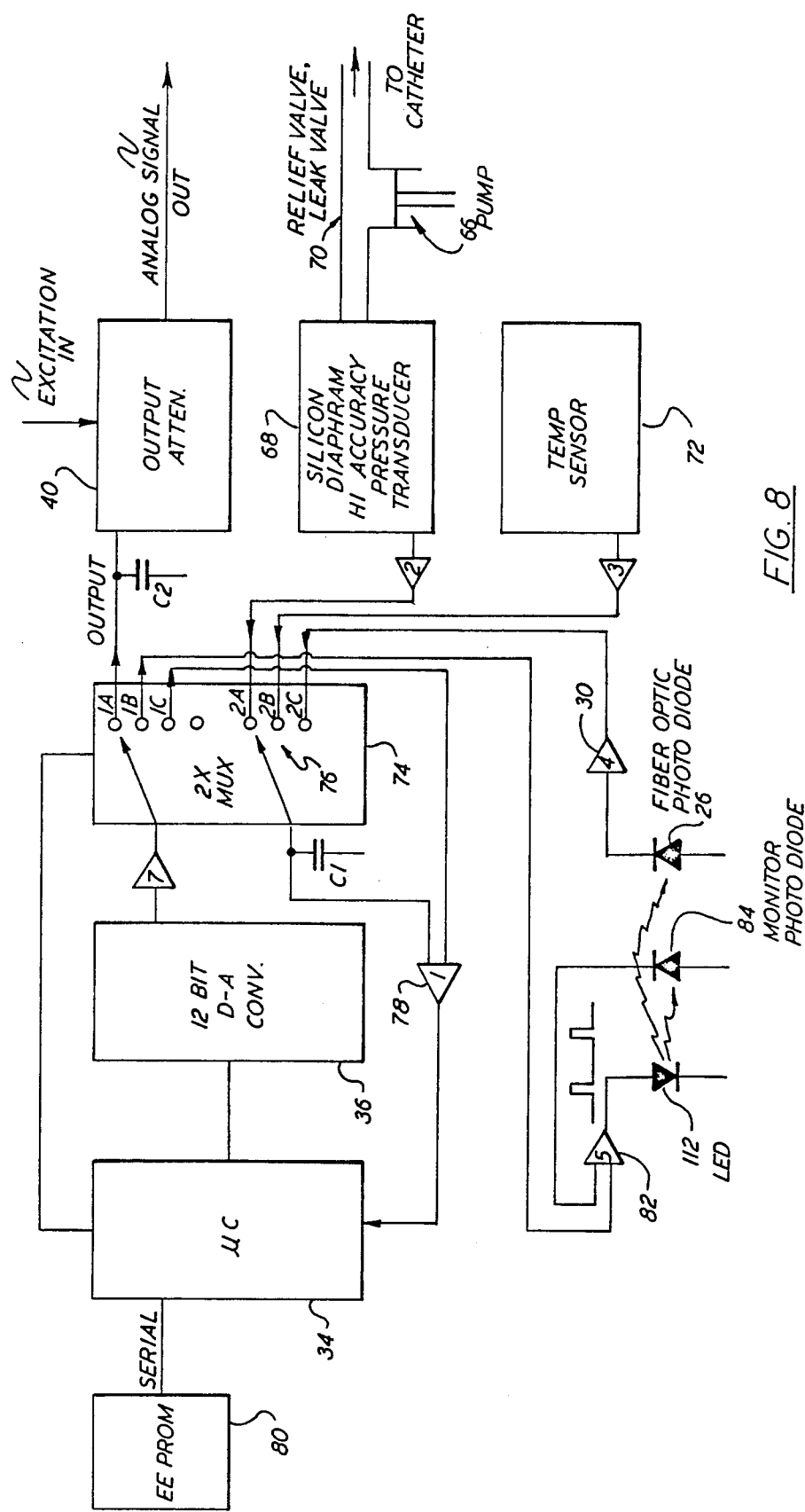
FIG. 8 is a partly schematic block diagram illustrating the operation of certain elements of the invention.

Initialization, calibration and operation of the system is effected through an electronic section illustrated in FIG. 8, some elements of which have been previously described. Upon application of excitation voltage microcomputer 34 automatically resets and initializes. The operator activates a vacuum pump, indicated diagrammatically at 66, connected to tubing 54 of the catheter. The interior of tube 54 will thus be brought to a sub-atmospheric pressure, including the area to which the interior surface of diaphragm 44 is exposed; as seen in FIGS. 4 and 5, the area on the interior of the diaphragm communicates with the area to which pump 66 is connected through spaces between the walls of ferrule 52 and tube 54.

The pressure within tube 54 is accurately measured and an electrical signal commensurate therewith is generated by silicon diaphragm pressure transducer 68. The vacuum is vented through leak valve 70. Temperature sensor 72 measures and generates an electrical signal commensurate with the temperature of the circuitry for compensation purposes. The outputs of pressure transducer 68, temperature sensor 72 and the previously described photo diode 26 are connected to MUX 74 and sequentially sampled by microcomputer 34, as indicated diagrammatically at 76 through comparator 78. Microcomputer 34 corrects the signal from precision transducer 68 to correct for temperature coefficient and computes the correction curve for the catheter at 10 mm/Hg intervals. EE PROM 80 stores the correction data for transducer 68, D to A converter 36, temperature sensor 72, offsets and output variable attenuator 40. Microcomputer 34 is programmed to recognize various conditions which would indicate possible incorrect calibration and to transmit a signal in response thereto (through D to A converter 36 to MUX 74) to operational amplifier 82 and LED 112. The resulting LED output is picked up by monitor photo diode 84 and the problem is indicated by a square wave on the monitor.

After completion of initialization and calibration, microcomputer 34 automatically shifts to the measuring mode. The microcomputer samples the signals from fiber optic photo diode 26 and temperature sensor 72 and routes the signal to output attenuator 40 at 300 samples per second. Capacitors C1 and C2 function as sample and hold capacitors. The output attenuator 40 modulates the excitation voltage to provide an accurate replica of the excitation to the input of the monitor at the standard 5 uv per mm of Hg. per volt of excitation. The output of LED 12 is measured by monitor photo diode 84 connected to amplifier 82, which compensates for changes in LED output with time and temperature. To increase the dynamic range of the system for variations in optical attenuation (such as an optical extension cable) the microcomputer controls the LED through the D-A by varying the bias on op-amp 82 which increases the LED output when optical attenuation is increased. The microcomputer uses double precision math which, combined with 12 bit conversion allows for a wide tolerance range in the manufacturing of the disposable part of the unit, e.g., ±20%. By allowing a wide design range on the disposable part of the unit the manufacturing cost is drastically reduced. This approach requires the described automatic calibration system, comprising the nondisposable portion of the unit. The automatic calibration system basically works by applying a known pressure to the back of the diaphragm through the catheter sheathing. This pressure is measured by a high precision silicone diaphragm pressure transducer contained in the nondisposable unit. The microcomputer contained within the nondisposable unit constructs a correction curve for the particular catheter attached to the unit. This gives the advantage of not only being able to manufacture the disposable portion to relatively wide tolerances but also negates the effect of possible long term instability caused, e.g., by extreme temperature exposure. For example, if the disposable catheters were to be exposed to high temperatures for an extended period of time, a zero drift in the catheter signal response could occur. By implementing a system where the disposable transducer is calibrated over its entire range just before usage, these effects are negated. Another advantage of using correction techniques will be the reduction of tolerances on parts in the disposable transducer, thus reducing the cost even further.

Examples of dimensions which may be used in the manufacture of the described catheter tips for intravenous blood pressure measurement applications, for a unit of number three French (one millimeter) in diameter, are as follows:

cap 42:
outside diameter 0.040"
length 0.120"
wall thickness 0.002"
diaphragm thickness 0.00025"
fiber 46:
diameter 0.010"
tubing 54:
outside diameter 0.036"
wall thickness 0.005"
holes 50:
diameter 0.0002"

What is claimed is:

1. A fiber optic pressure transducer comprising:
 (a) light generating means;
 (b) an elongated, optical fiber having a first terminal end positioned to receive light from said generating means and a second terminal end to which said light is carried through said fiber;
 (c) a deformable member having a first, light reflecting surface positioned in opposed, spaced relation to said second terminal end and movable with respect thereto in accordance with the pressure exerted on the opposite side of said deformable member from first surface;
 (d) a layer of light absorptive material interposed between said second terminal end and said light reflecting surface and having a plurality of openings therethrough, whereby a portion of said light carried through said fiber to said second terminal end passes through said openings and another portion is intercepted by said layer, and a portion of the light passing through said openings and reflected by said reflecting surface passes back through said openings and is carried back through said fiber and another portion is intercepted by said layer; and
 (e) means for generating an electrical signal commensurate with the intensity of light carried back through said fiber, said intensity being a function of the distance between said second terminal end of said fiber and said reflecting surface and thereby of said pressure exerted on said opposite side of said deformable member.

2. The invention according to claim 1 wherein said layer is carried directly upon said second terminal end of said fiber.

3. The invention according to claim 2 wherein said layer comprises a photo-resist layer applied directly to said second terminal end.

4. The invention according to claim 1 wherein said means for generating an electrical signal comprises a photo diode arranged to receive said light carried back through said fiber.

5. The invention according to claim 4 and further comprising a hollow, flexible tube through which said fiber extends.

6. The invention according to claim 5 and further including a hollow cap engaged with said tube to enclose said second terminal end of said fiber.

7. The invention according to claim 6 wherein said deformable member comprises an end closure of said cap.

8. The invention according to claim 7 and further comprising means fixedly engaging said fiber adjacent said second terminal end and positioned within said cap to hold said second terminal end in a predetermined position relative to said reflecting surface.

9. The invention according to claim 8 wherein said means fixedly engaging said fiber comprises a ferrule having a central opening wherein said fiber is glued.

10. The invention according to claim 9 wherein said ferrule includes a terminal engaged with an internal surface of said cap for establishing the relative positions of said second terminal end of said fiber and said reflecting surface.

* * * * *